United States Patent [19]

Tomesch

[11] 4,366,154

[45] Dec. 28, 1982

[54] TROPYL DERIVATIVES

[75] Inventor: John C. Tomesch, Succasunna, N.J.

[73] Assignee: Sandoz, Inc., East Hanover, N.J.

[21] Appl. No.: 319,254

[22] Filed: Nov. 9, 1981

[51] Int. Cl.³ .................... A61K 31/46; C07D 451/02; C07D 513/14; A61K 31/54
[52] U.S. Cl. ..................... 424/247; 424/265; 544/43; 546/125; 546/132
[58] Field of Search .................. 544/43; 546/125, 132; 424/247, 265

[56] References Cited

U.S. PATENT DOCUMENTS 2,800,476  7/1957  Stoll et al. ........................... 546/132
3,987,042  10/1976  Gueremy et al. ..................... 544/43

Primary Examiner—Henry R. Jiles
Assistant Examiner—Bernard Dentz
Attorney, Agent, or Firm—Gerald D. Sharkin; Richard E. Vila; Frederick H. Weinfeldt

[57] ABSTRACT

Tropyl derivatives of the formula:

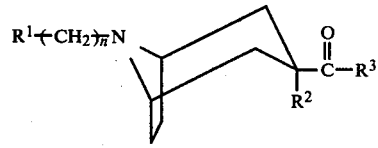

in which $R^1$ is (a) phenyl linked through a direct bond, —O—,

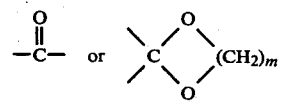

(in which m=2 or 3); (b) diphenylmethyl; or (c) 10H-phenothiazin-10-yl; (each of which type may be substituted, or unsubstituted); $R^2$ is —H, —OH, or —O Si $(CH_3)_3$; and $R^3$ is substituted or unsubstituted phenyl, e.g. 4-[3-(4-fluorobenzoyl)-8-azabicyclo [3.2.1]oct-8-yl]-1-(-4-fluorophenyl)-1-butanone, in free base form or pharmaceutically acceptable acid addition salts are useful as pharmaceuticals.

19 Claims, No Drawings

TROPYL DERIVATIVES

This invention relates to tropyl derivatives, and more particularly to 3,8-disubstituted-8-azabicyclo[3.2.1]oct-3-yl derivatives and to their use as pharmaceutical agents as well as to pharmaceutical compositions containing such compounds.

The compounds involved in this invention are conveniently represented by the formula I:

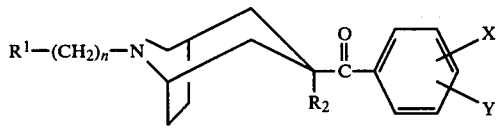

wherein
each of X and Y is independently, a hydrogen atom, halo having an atomic weight of from about 18 to 80, i.e. fluoro, chloro or bromo; alkyl or alkoxy having from 1 to 4 carbon atoms, or trifluoromethyl, provided that when X and Y are trifluoromethyl, branched alkyl, or branched alkoxy, they are not on adjacent carbon atoms;

wherein n is a whole number of from 1 to 4, preferably 3; $R^1$ is of type:

(a) a radical of the formula

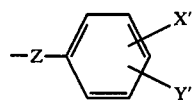

wherein
each of X' and Y' is independently, a hydrogen atom, halo having an atomic weight of from about 18 to 80, i.e. fluoro, chloro or bromo; alkyl or alkoxy having from 1 to 4 carbon atoms, or trifluoromethyl, provided that when X' and Y' are trifluoromethyl, branched alkyl or branched alkoxy they are not on adjacent carbon atoms, and Z is

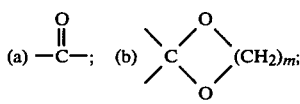

(c) —O—; or (d) a direct bond, wherein m is 2 or 3, preferably 2;

(b) a radical of the formula:

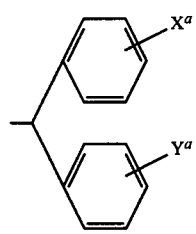

in which $X^a$ and $Y^a$ are, independently, a hydrogen atom or fluoro; or (c) a radical of the formula:

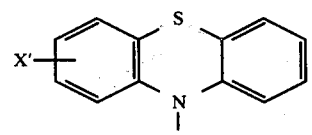

in which X' is defined above; and,
$R^2$ is
(a) a hydrogen atom;
(b) —OH; or
(c) —O—Si(CH$_3$)$_3$ Compounds I may be considered as including two general classes of compounds depending on the nature of $R^2$, i.e. Compounds Ia in which $R^2$ is of type (a) i.e. a hydrogen atom, and compounds Ib in which $R^2$ is of type (b) i.e. a hydroxy function. In addition, either of the above-defined classes may be further divided depending on the nature of $R^1$, i.e. compounds Ia-1 and Ib-1 in which $R^1$ is other than of type (c), i.e. $R^1$ is of types (a) or (b), and compounds Ia-2 and Ib-2 in which $R^1$ is of type (c), i.e. a phenothiazine radical.

Methods of preparing compounds of classes Ia and Ib are presented in Reaction Schemes A and B, below. In these reaction schemes, X, Y and n are as defined above. In Reaction Scheme B, it will be noted that compounds I where $R^2$ is of type (c) are designated as compounds Ic.

REACTION SCHEME A

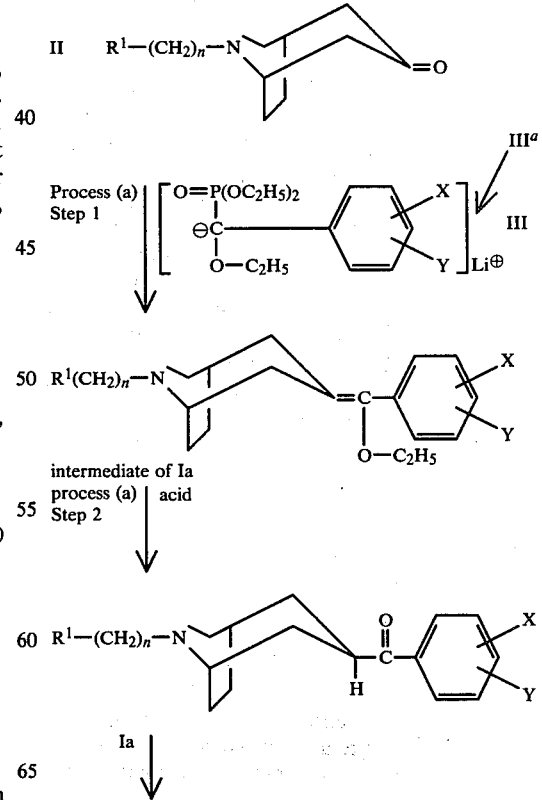

REACTION SCHEME B

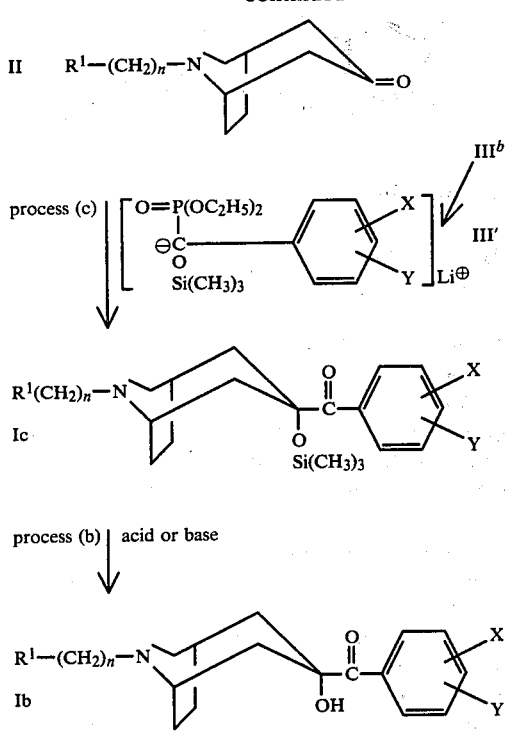

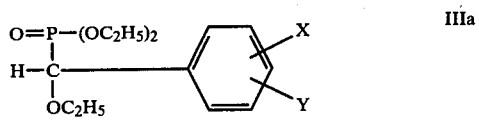

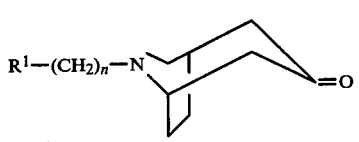

Process (a) may be carried out under the conditions generally observed for performing a Wittig reaction. For example, by first preparing a compound III, i.e. a lithium salt of a phosphonate reagent of the formula III$^a$

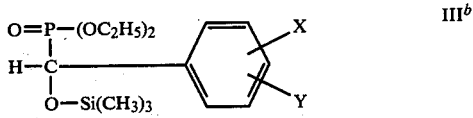

in which X and Y are as defined, by treating a compound III$^a$ with a lithium organometallic reagent, such as lithium alkyl having from 3 to 8 carbon atoms, e.g. n-butyl lithium in an inert medium, e.g. an ether preferably a cyclic ether such as tetrahydrofuran, or an acyclic ether, such as dimethoxyethane, under essentially anhydrous conditions, at reduced temperatures, e.g. at from about −60° to −100° C., preferably at about −60° to −75° C., and then reacting such a lithium salt in situ with a tropanone compound of the formula II

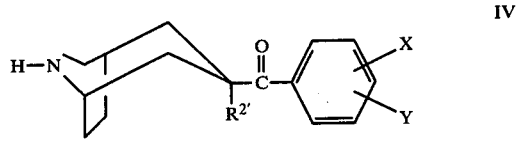

in which R$^1$ and n are as defined below, initially at reduced temperatures, e.g. at from about −60° to −100° C., such as from about −65° to −75° C., and then gradually warming to a moderate temperature, e.g. 20° to 80° C., to form an enol ether intermediate product.

The intermediate product is then hydrolyzed by treatment with aqueous acid, e.g., diluted hydrochloric acid at moderate temperatures, e.g. at from about 20° to 30° C., to yield the corresponding compound Ia.

In process (b), a compound Ic is hydrolyzed by treatment with aqueous acid or base, e.g. dilute aqueous sodium hydroxide at moderate temperatures e.g. from about 20° to 60° C., to obtain the corresponding compound Ib.

Compounds Ic are obtainable by process (c). Process (c) involves reacting the lithium salt of a siloxy-bearing phosphonate reagent i.e. a compound of formula III$^b$

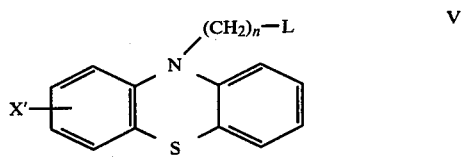

in which X and Y are as defined, with a compound II in an inert medium, e.g. an ether, preferably a cyclic ether, such as tetrahydrofuran, or an acyclic ether, such as dimethoxyethane, under essentially anhydrous conditions, at initially a reduced temperature, e.g. at from about −80° to −100° C., e.g. from about −95° to −100° C., then warmed to from about 20° to 60° C., e.g. to from about 20° to 30° C. to yield a corresponding compound Ic.

Lithium salts (compounds III') employed in process (b) may be obtained by conventional means for forming an organo-lithium salt, e.g. by treatment of a compound IIIb with lithium diisopropyl amide, under essentially anhydrous conditions, in an inert organic medium, e.g. an ether, preferably a cyclic ether such as tetrahydrofuran, or an acyclic ether such as dimethoxyethane, at reduced temperatures e.g. about −60° to −80° C. It is preferred to react a compound III' in situ, utilizing the same medium for the preparation of such compound III' and process (c).

A convenient method of preparing compounds I in which R$^1$ is of type (c) and R$^2$ is H or —OH, i.e. compounds Ia-2 or Ib-2 comprises reacting a compound of formula IV:

IV

[structure: H—N ring—C(=O)(R$^{2'}$)—phenyl with X, Y]

in which X and Y are as defined above and R$^{2'}$ is either —H or —OH; with phenothiazine derivative of the formula V

V

[structure: phenothiazine with (CH$_2$)$_n$—L on N, X' substituent]

in which X' and n are as defined above, and L is a leaving group, such as a halo having an atomic weight of from about 34 to 127, i.e. Cl, Br or I, preferably Cl, or a sulfonic acid derivative, such as a p-toluene sulfonate (process (d)). Compounds IV are obtainable by "dealkylating" a 8-methyl tropyl compound of formula VI:

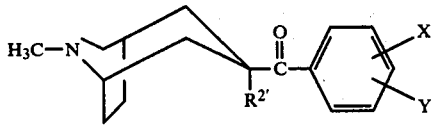

in which X, Y and R²' are as defined above, (process (e)).

The preparation of compounds Ia-2 and Ib-2 are conveniently depicted in Reaction Scheme C below in which n, R²', X, Y, X' and L are as defined above.

REACTION SCHEME C

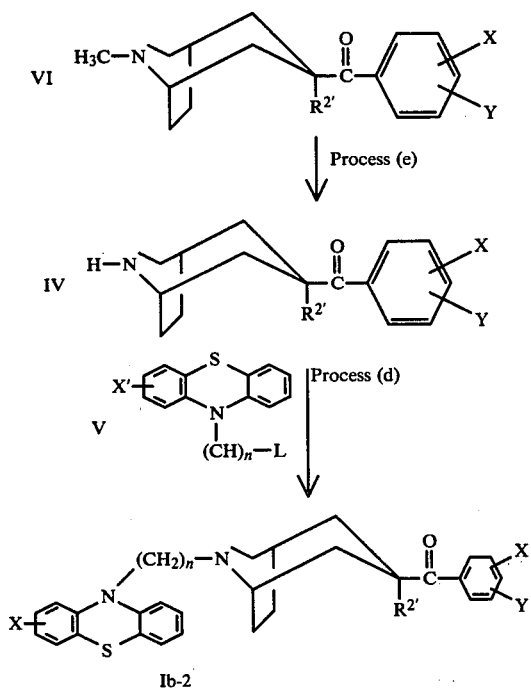

In process (d), a compound IV is reacted with a compound V, preferably under essentially anhydrous conditions, in the presence of an acid acceptor, e.g. sodium carbonate, in an inert organic medium, e.g. a lower alkanol i.e. having from 1 to 4 carbon atoms such as ethanol, at e.g. temperatures of from about +30° to +120° C., such as at the reflux temperature of the medium.

Process (e) may be carried out by known means for dealkylating a tertiary amine. For example, the method of U.S. Pat. No. 3,905,981 would involve reaction of a compound VI with a vinyl haloformate to form the corresponding vinyloxycarbonyl amide, which is then cleaved under mild acidic hydrolytic conditions to obtain the corresponding compound IV. Alternatively, process (e) may be carried out by a two step procedure wherein first a compound VI is reacted with 2,2,2-trichloroethyl chloroformate in the presence of an acid acceptor, such as a small amount of potassium carbonate, in an inert medium, e.g. an aromatic hydrocarbon such as toluene, under essentially anhydrous conditions, at moderate temperatures, e.g. from about 20° to 60° C., particularly 20° to 30° C., to form an 8-trichloroethoxyformyl-bearing intermediate which is then treated in the second step. In the second step, the resulting intermediate is treated with zinc dust and glacial acetic acid, preferably under essentially anhydrous conditions, at moderate temperatures, e.g. 20° to 60°, particularly 20° to 30° C.; the glacial acetic acid serving as the reaction medium.

The final products and intermediate compounds described herein may be recovered and refined, where such is desired, by conventional means, such as by crystallization, distillation or chromatographic techniques such as column or thin layer chromatography.

Reagents and starting materials described herein, e.g., compounds II, III$^a$, III$^b$, IV, V, and VI are known and obtainable by known means, or where not known, may be obtained by adaptation of methods reported in the literature for the preparation of known analogs; some compounds being commercially available. For example, compounds II may be prepared by adaptation of the methods described in *J. Org. Chem.* 36, 1718 (1971), while compounds I and VI may be prepared by adaptation of the procedures described in *Liebigs Ann. Chem.*, 88–100 (1977), *J. Org. Chem.* 45, 3994–3998 (1980), and *J.A.C.S.* 82, 151 (1960).

Preferred compounds Ia-1 and Ib-1 are those having one or more of the following characteristics:

(1) that any substituents i.e. X, Y, X', Y', X$^a$ and Y$^a$ on phenyl radicals are at other than ortho-positions, (2) that any of X, X', X$^a$ or Y$^a$ are located at the para-position.

(3) that when any substituent is halo, it is preferably fluoro.

Preferred compounds Ia-2 and Ib-2 are those in which X' is chloro or trifluoromethyl.

It will be understood that certain portions of compounds I are less stable than other portions, and that it is prudent to employ particular techniques, or moderate reaction conditions to minimize conversions away from the desired products in various processes. For example, when Z is of type (b), e.g. a ethylenedioxy function, it is prudent to minimize acidic conditions which will convert such unit to a carbonyl group. Similarly, compounds I in which R² is of type (c), i.e. compounds Ic may be converted to compounds Ib, as is depicted in Reaction Schemes B; hence, it is prudent to minimize exposure to aqueous acidic or basic (nucleophilic) solutions and other known silyl ether cleaving conditions, where a compound Ic is desired as final product, rather than as an intermediate of a corresponding compound Ib. On the other hand, one or the other, or both such types of functions may be cleaved selectively, by judicious choice of reaction conditions or sequence of process steps.

It will be appreciated that since compounds I have a tropyl nucleus, the substituents at the 3-position can be in an α or β relationship with respect to the tropyl nucleus. While both the 3α- and 3β-forms are contemplated as included within this invention, the β-forms are preferred, and the products of the examples presented hereinafter are essentially in the β-form, i.e. the benzoyl-type units are at the 3β-position, whereas R² is at the 3α-position.

As will be appreciated, compounds I have a tertiary nitrogen atom which renders them capable of forming acid addition salts. Accordingly, non-toxic pharmaceutically acceptable acid addition salts of compounds I constitute an embodiment of this invention. Such acid addition salts may be prepared in the conventional manner, e.g. by treatment of a compound I with a suitable acid. Conversely, compounds I may be obtained from their acid addition salts by neutralization and extraction, by known means. Such acid addition salts are useful for the same utilities and in the same equivalent amounts as compounds I, as described hereinafter.

STATEMENT OF UTILITY

The compounds of formula I of this invention are useful as pharmaceuticals in animals. In particular, the compounds of formula I are useful as neurolepic agents as indicated by the Spiroperidol Receptor Binding Assay in accordance with the method basically described in I. Creese et al. in Science 192: 481-83 (Apr. 30, 1976) and in Nature 270: 180-82 (November, 1977).

Routine and non-substantive modifications of the Spiroperidol Receptor Binding Assay that are evident from the following description are employed in such evaluation in which non-radioactive compounds are tested for their ability to displace $^3$H-spiroperidol binding to isolated calf dopamine receptors. An aliquot of frozen calf caudate dopamine tissue is thawed and diluted with 0.05 M Tris buffer containing metal ions (120 mM NaCl, 5 mM KCl, 2 mM CaCl$_2$ and 1 mM MgCl$_2$) to a final concentration of 16 mg/ml, i.e., a 12.5 fold dilution. This suspension is made homogenous by homogenation with a Brinkmann Polytron using a rheostat setting of 8 for 10 seconds. Ten $\lambda$ of $^3$H-spiroperidol solution is diluted in 0.05 M Tris buffer (pH 7.1 at 37° C.) to give a concentration of 10 nM ($3.96 \times 10^{-9}$ g/ml). This solution is defined as "working stock" solution. This solution is further diluted in 0.05 M Tris buffer to give a final "working" solution of 3 nM. Both of these solutions are stored frozen at $-20°$ C., while the stock $^3$H-spiroperidol solution in ethanol is kept refrigerated at $+2°$ C. Periodically, the stock ethanolic $^3$H-spiroperidol solution is examined by TLC for chemical purity. If the purity becomes <90%, the stock solution is repurified or new high purity $^3$H-spiroperidol is obtained and the impure $^3$H-spiroperidol discarded. A 0.1 ml portion of 3 nM $^3$H-spiroperidol "working" solution is added to a $12 \times 75$ mm borosilicate disposable test tube along with 0.1 ml of freshly prepared 50% ethanol solution. This is the control tube for measuring total binding. Non-specific binding is determined by the addition of 0.1 ml of $10^{-5}$ M (+)-butaclamol (in 50% ethanol) to other tubes in the place of 0.1 ml 50% ethanol. The specific binding is determined in the final results by substraction of the non-specific binding from the total binding. All compounds screened have their results expressed in terms of specific binding. All compounds screened are tested at a final concentration of $5 \times 10^{-6}$ M.

For simplicity and expedience, it is assumed that all compounds have an average molecular weight of 300 a.m.u. Three mg of a compound are placed in $18 \times 150$ mm borosilicate disposable test tubes. These tubes are kept in the dark at room temperature until the day of the assay at which time 10 ml of absolute ethanol is added and the tubes placed in a Branson Ultrasonic Cleaner for 15 minutes and then vortexed in order to put the compounds into solution. All tubes are closely examined to make certain the compounds are completely in solution. If not, then 3 drops of 2 N HCl is added. If the compound(s) are still not in solution but a cloudy homogenous suspension is found, then the subsequent dilutions are continued. If large insoluble particles are found, then each compound is tested separately at a later time. This gives a concentration of $\sim 1 \times 10^{-3}$ M. The compounds are further diluted by serial dilution as follows: 0.1 ml of the $10^{-3}$ M solution is added to 1.9 ml of 50% ethanol and vortexed. 0.1 ml of this solution is added to $12 \times 75$ mm test tubes for assay. All assays are run in duplicate. A 0.8 ml portion of caudate tissue suspension is added to all tubes, vortexed, incubated at 2° C. for 120 minutes, and rapidly filtered under vacuum through Whatman GF/B glass fiber filters. Each tube is rinsed once with 3 ml ice-cold 50 mM Tris buffer (pH 7.1 at 37° C.) and the filter subsequently washed once with 6 ml of the same Tris buffer. The $^3$H-spiroperidol trapped on the filters is counted by liquid scintillation counting on a Beckman LS 8000 after the filters were rapidly shaken for 45 minutes in the scintillation vials with 10 ml of scintillation cocktail. Results of compounds screened are calculated by the on line data reduction system in the Beckman LS 8000 and results expressed as percent specifically bound compared to control.

After the initial activity of a compound is found it is then examined at various concentrations in order to ascertain its potency in displacing 3H-spiroperidol at the dopamine receptor. These results are expressed as the IC$_{50}$, the concentration of drug which inhibits 50% of the specific 3H-spiroperidol binding.

Dopamine receptors are obtained from male Holstein calves. Immediately after exsanguination, the brains are quickly removed and placed in ice. Dissection of the caudate nucleus is completed within 2 hours after sacrifice and the tissue weighed, and homogenized (1:10, W/V) in 0.05 M Tris buffer (pH 7.1 at 37° C.) using a Brinkmann Polytron for 10 seconds with a rheostat setting of 8. The homogenate is centrifuged for 10 minutes at 20,000 RPM in a Sorvall RC2B centrifuge using a SS 34 head. The supernatant is decanted and the pellet washed twice to remove endogenous dopamine by resuspension with the use of the Brinkmann Polytron and recentrifugation. The final pellet is resuspended in 0.05 M Tris (pH 7.1 at 37° C.) containing 120 mM, NaCl, 5 mM KCl, 2 mM CaCl$_2$, and 1 mM MgCl$_2$ in a final concentration of 200 mg wet weight starting material/ml of buffer. The homogenate is stored in 4 ml aliquots in glass bottles in liquid nitrogen.

The compounds of the formula I exhibit a relatively high potency in displacing 3H-spiroperidol binding in the above-indicated test and hence possess an interesting and desirable type of anti-psychotic activity. For such use the amount of the compounds of the formula I to be administered will vary depending upon the compound used, mode of administration, the condition being treated, the severity of the condition and other known factors. However, in general satisfactory results are obtained when administered to a host mammal at a daily dosage of from 0.3 to 100 milligrams per kilogram of body weight, preferably given orally and in divided doese 2 to 4 times a day, or in sustained release form. For larger mammals, the administration of from 10 to 500 milligrams per day provides satisfactory results and dosage forms for internal administration may comprise from 5 to 250 milligrams of the compound in admixture with a solid or liquid carrier. The daily dosage for larger mammals is preferably from 30 to 200 milligrams and dosage forms preferably contain from 7.5 to 100 milligrams.

Pharmaceutical compositions provided by the invention and useful for effecting tranquilization of mammals contain a compound of the formula I as active ingredient and one or more conventional pharmaceutically acceptable carriers, including such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compositions of the invention adapted for oral or parenteral administration may contain from 1% to 90% by total weight of active ingredient in combination with the carrier, more usually 3% to 60%. The preferred unit dosage forms are the essentially solid forms adapted for oral administration. When the carrier is a liquid it is preferred that a suspending agent or an emulsifying agent be present.

A representative formulation for administering 3 to 4 times a day or as needed in treatment of anxiety and/or tension is a capsule prepared by conventional capsulating techniques and containing the following ingredients:

| Ingredient | Weight in mg. |
|---|---|
| 4-[3-(4-fluorobenzoyl)-8-azabicyclo[3.2.1]oct-8-yl]-1-(4-fluorophenyl)-1-butanone | 20 |
| Lactose | 200 |

The following examples are illustrative of the invention. All temperatures are centigrade and room temperature is 20° to 30° C., unless indicated otherwise. The compounds I obtained by these examples are in essentially the β-isomeric form (R² is in the α-configuration).

EXAMPLE 1

4-[3-(4-Fluorobenzoyl)-8-azabicyclo[3.2.1]oct-8-yl]-1-(4-fluorophenyl)-1-butanone (a compound Ia-1)

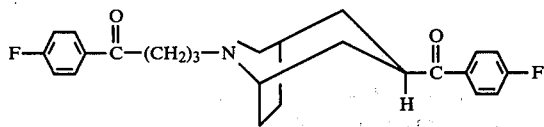

Step A Preparation of 8-{3-[2-(4-fluorophenyl)-1,3-dioxolan-2-yl]-propyl}-8-azabicyclo [3.2.1]octan-3-one (a compound II)

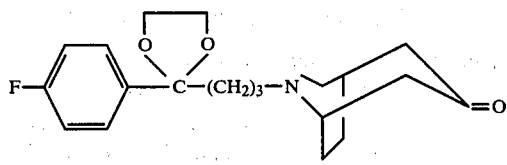

To a flask equipped with a nitrogen gas inlet, addition funnel and magnetic stirrer is charged 2.7 g. (0.025 mol) of 2,6-cycloheptadienone and 90 ml. of methanol. The solution is stirred and 5.63 g. (0.025 mol) of 2-(4-fluorophenyl)-1,3-dioxolane-2-propanamine in 90 ml. of methanol is added over 30 minutes. After the addition, the reaction is allowed to stir for 20 hrs. The solution is then concentrated in vacuo to afford an oil. Chromatography on 500 g. of silica gel gives, after evaporation of solvent, 8-{3-[2-(4-fluorophenyl)1,3-dioxolan-2-yl]-propyl}-8-azabicyclo-[3.2.1]octan-3-one as an oil.

Step B, Preparation of 4-[3-(4-fluorobenzoyl)-8-azabicyclo[3.2.1]oct-8-yl]-1-(4-fluorophenyl)-1-butanone To a flask equipped with a magnetic stirrer, low temperature thermometer, addition funnel, serum cap and nitrogen gas inlet on top of a reflux condenser, is added 100 ml. of dry tetrahydrofuran and 3.18 g. (0.011 mol) of diethyl 1-ethoxy-1-(4-fluorophenyl)methane phosphonate. The resultant solution is stirred while the flask is cooled in a dry ice-isopropanol bath until the internal temperature is −70° C., at which time 6.9 ml. (0.011 mol) of 1.6 N n-butyl lithium is added over two minutes. After stirring 20 minutes, a yellow solid precipitates from the solution.

To the resulting suspension is added dropwise with stirring, a solution of 3.33 g. (0.01 mol) 8-[3-[2-(4-fluorophenyl)-1,3-dioxolan-2-yl]propyl]-8-azabicyclo[3.2.1]octan-3-one in 50 ml. dry tetrahydrofuran over 20 minutes while the reaction temperature is maintained between −65° C. to −75° C. The cold reaction mixture is then permitted to stir for 1½ hours, then allowed to warm to room temperature, after which it is placed in an oil bath at +60° to 65° for 4 hours. After standing for about 16 hours, 50 ml. of water and 100 ml. of diethyl ether is added and following agitation the layers are partitioned. The aqueous solution is extracted two additional times with diethyl ether and all ethereal extracts are combined, dried over anhydrous sodium sulfate and concentrated to afford a viscous oil. The oil is dissolved in 300 ml. of acetone, 20 ml. of 1.2 N hydrochloric acid is added and the solution stirred for 4 hours. The solution is concentrated in vacuo, 100 ml. of 3 N hydrochloric acid is added and the solution is extracted with 150 ml. of diethyl ether. The hydrochloric acid solution is made basic with 15% sodium hydroxide aqueous solution, then extracted three times with 100 ml. portions of diethyl ether.

The combined ethereal solutions are dried over anhydrous sodium sulfate and concentrated in vacuo to afford a yellow oil, which upon recrystallization from hexanes affords crude 4-[3-(4-fluorobenzoyl)-8-azabicyclo[3.2.1]oct-8-yl]-1-(4-fluorophenyl-1-butanone (ivory-colored) m.p. 96°–98.5° C. After, an additional recrystallization refined product is obtained with a melting point of 99.5°–101° C.

EXAMPLE 2

Repeating the procedure of Step A of Example 1, but using in place of the 2-(4-fluorophenyl)-1,3-dioxolane-2-propamine used therein, an approximately equivalent amount of:
(a) 4,4-bis(4-fluorophenyl)butylamine;
(b) 3-(2-chloro-10H-phenothiazin-10-yl)-propylamine;
(c) 3-(4-methoxyphenoxy)propylamine; or
(d) benzylamine;
there is accordingly obtained: as compounds II:
(a) 8-[4,4-bis(4-fluorophenyl)butyl]-8-azabicyclo[3.2.1]octan-3-one;
(b) 8-[3-(2-chloro-10H-phenothiazin-10-yl)propyl]-8-azabicyclo[3.2.1]octan-3-one;
(c) 8-[3-(4-methoxyphenoxy)propyl]-8-azabicyclo[3.2.1]octan-3-one; and
(d) 8-benzyl-8-azabicyclo[3.2.1]octan-3-one.

EXAMPLE 3

Repeating the procedure of Step B of Example 1, but using in place of the 8-{3-[2-(4-fluorophenyl)-1,2-dioxolan-2-yl]propyl}-8-azabicyclo[3.2.1]octan-3-one used therein as compounds II, the products (b), (c) or (d) of Example 2, above, there is accordingly, respectively, obtained the following compounds Ia:

(a) 8-[3-[2-chloro-(10H-phenothazin-10-yl)propyl]-8-azabicyclo[3.2.1]-oct-3-yl]4-fluorophenyl methanone, as a glassy solid;

(b) 8-{[3-(4-methoxyphenoxy)propyl]-8-azabicyclo[3.2.1]-oct-3-yl}4-fluorophenyl methanone; and (c) (8-benzyl-8-azabicyclo[3.2.1]-oct-3-yl)4-fluorophenyl methanone, m.p. 232°-234° (d).

EXAMPLE 4

{8-[3-(4-methoxyphenoxy)propyl]-3-hydroxy-8-azabicyclo[3.2.1]oct-3-yl}4-fluorophenyl methanone

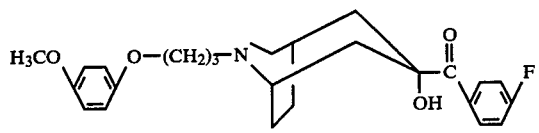

Step A, preparation of {8-[3-(4-methoxyphenoxy)propyl]-3-trimethylsiloxy-8-azabicyclo[3.2.1]oct-3-yl}4-fluorophenyl methanone

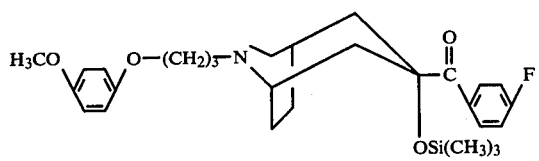

To a flask equipped with a magnetic stirrer, low temperature thermometer, addition funnel, serum cap and nitrogen gas inlet is placed 90 ml. of dry tetrahydrofuran and 1.40 ml. (1.01 g, 0.01 mol.) of diisopropyl amine. The resultant solution is stirred while the flask is cooled in a dry ice-methanol bath until the internal temperature is −60°, at which time 6.25 ml. (0.01 mol) of 16 N n-butyllithium is added, over one minute. After stirring for 30 minutes at between −60° to −70°, 3.34 g. (0.01 mol) of diethyl 1-(trimethylsiloxy)-1-(4-fluorophenyl)methane phosphonate is added over one minute. The resulting yellow-green solution is stirred for 20 minutes then cooled to −100° by adding liquid nitrogen to the methanol bath. 2.51 g (0.0087 mol) of 8-[3-(4-methoxyphenoxy)propyl]-8-azabicyclo[3.2.1]-octan-3-one in 35 ml. of dry tetrahydrofuran is added dropwise over 5 minutes, while the temperature is maintained between −85° to −100°. This solution is stirred at this temperature for an additional 30 minutes then allowed to warm to room temperature and stirred for 18 hours. The solution contains the title product of this step and is retained for use in Step B, below. However, if desired the product may be recovered by neutralizing the solution, then removing the solvent, under vacuum and then refining the product by recrystallization or chromatography, being careful to minimize contact with aqueous acidic or basic conditions.

Step B, Preparation of {8-[3-(4-methoxyphenoxy)propyl]-3-hydroxy-8-azabicyclo[3.2.1]oct-3-yl}4-fluorophenyl methanone 9 ml. of an aqueous solution containing 0.70 g (0.0174 mol) of sodium hydroxide is added and the solution obtained in Step A, above, stirred for 7 hours. Sodium chloride is added to saturate the aqueous solution followed by 100 ml. of diethyl ether. The solution is agitated, the layers partitioned, and the ethereal solution is dried over anhydrous sodium sulfate. The solution is concentrated in vacuo to afford a yellow oil. After drying on a vacuum pump for 3 hours, the oily solid is recrystallized from 300 ml. of a hot mixture of hexane isomers. The resulting solid is recrystallized from 100 ml. of hot hexanes to afford the title product, {8-[3-(4-methoxyphenoxy)propyl]-3-hydroxy-8-azabicyclo-[3.2.1]oct-3-yl}-4-fluorophenyl methanone; m.p. 100°-101° C.

EXAMPLE 5

((8-{3-[2-(4-Fluorophenyl)-1,3-dioloxan-2-yl]propyl}-3-trimethylsiloxy-8-azabicyclo[3.2.1]-oct-3-yl))phenyl methanone (a Compound Ic)

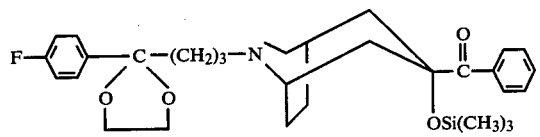

Repeating the procedure of Step A of Example 4 but employing in place of the 8-[3-(4-methoxyphenoxy)-propyl]-8-azabicyclo[3.2.1]octan-3-one used therein, an approximately equivalent amount of 8-{3-[2-(4-fluorophenyl)-1,3-dioxolan-2-yl-]propyl}-8-azabicyclo[3.2.-1]octan-3-one; there is accordingly obtained ((8-{3-[2-(4-fluorophenyl)1,3-dioxolan-2-yl]propyl}-trimethylsiloxy-8-azabicyclo[3.2.1]oct-3-yl)) phenyl methanone (as an oil).

EXAMPLE 6

8-[4,4-Bis(4-fluorophenyl)butyl]-3-hydroxy-8-azabicyclo[3.2.1]oct-3-yl phenyl methanone Repeating the procedure of Step A of Example 4 but employing in place of the 8-[3-(4-methoxyphenoxy)-propyl]-8-azabicyclo[3.2.1]octan-3-one used therein, an approximately equivalent amount of 8-[4,4-bis(4-fluorophenyl)butyl]-8-azabicyclo[3.2.1]octan-3-one; there is accordingly obtained (as a compound Ic) 8-[4,4-bis(4-fluorophenyl)butyl]3-trimethylsiloxy-8-azabicyclo[3.2.-1]oct-3-yl phenyl methanone, (m.p. 111°-113°), which upon treatment according to the procedure of Step B of Example 4, yields accordingly, 8-[4,4-bis(4-fluorophenyl)butyl]-3-hydroxy-8-azabicyclo[3.2.1]oct-3-yl phenyl methanone, (as an oil).

EXAMPLE 7

{8-[3-(2-Chloro-10H-phenothiazine-10-yl)propyl]-8-azabicyclo[3.2.1]oct-3-yl}4-fluorophenyl methanone

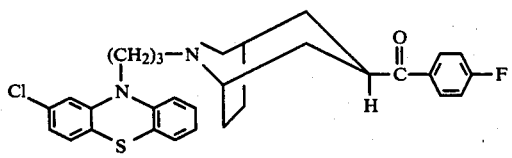

Step A, Preparation of
8-(azabicyclo[3.2.1]oct-3-yl)-4-fluorophenyl methanone

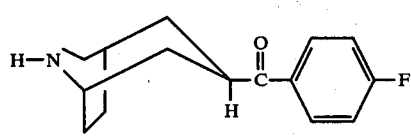

In a flask equipped with a magnetic stirrer and nitrogen gas inlet, is placed 0.495 g. (0.002 mol) of 8-methyl-8-(azabicyclo[3.2.1]-oct-3-yl) 4-fluorophenyl methanone, 15 ml. of toluene and a trace of potassium carbonate. To this is added 0.31 ml. (0.477 g., 0.0021 mol) of 2,2,2-trichloroethyl chloroformate and the reaction is permitted to stir for 18 hours. Following this period, water is added and the mixture is extracted three times with 25 ml. portions of methylene chloride. The methylene chloride solution is dried over anhydrous sodium sulfate and then concentrated in vacuo to afford 8-(2,2,2-trichloroethoxyformyl)-8-(azabicyclo[3.2.1]oct-3-yl) 4-fluorophenyl methanone.

In a flask equipped with a magnetic stirrer and nitrogen gas inlet is placed 0.84 g (0.0021 mol) of 8-(2,2,2-trichloroethoxyformyl)-8-(azabicyclo[3.2.1]oct-3-yl) 4-fluorophenyl methanone, 25 ml. of glacial acetic acid and 0.50 g. of zinc dust. The mixture is stirred at room temperature for 18 hours, then filtered and neutralized with dilute aqueous sodium hydroxide solution. The aqueous solution is extracted three times with methylene chloride and the organic solution dried and concentrated in vacuo to afford crude product of this step. The product is decolorized using activated charcoal in hexane and then purified by column chromatography on silica gel with 30% methanol-70% chloroform as the eluent. The desired product is purified by dissolving in methylene chloride, filtering the solution and concentrating in vacuo. This procedure is repeated with diethyl ether and finally with hot hexane. Concentration of this affords 8-(azabicyclo[3.2.1]oct-3-yl)-4-fluorophenyl methanone, m.p. 85°–89° C.

Step B, Preparation of
{8-[3-(2-chloro-10H-phenothiazin-10-yl)propyl]-8-azabicyclo[3.2.1]oct-3-yl}4-fluorophenyl methanone In a flask equipped with a magnetic stirrer and a reflux condenser with a nitrogen gas inlet is placed 2.33 g of the product of step A, above, 2.76 g of 10-(3-chloropropyl)-2-chlorophenothiazine, 0.90 g of sodium bicarbonate and 100 ml. of ethanol. The mixture is refluxed for about 18 hrs. and then permitted to cool to room temperature. Following concentration in vacuo the residue is taken up in methylene chloride and extracted with water. The organic solution is dried over sodium sulfate and then evaporated under reduced pressure. The resulting material is refined with a short silica gel column using 10% ethanol-methylene chloride to remove very non-polar and polar impurities and the eluate submitted for high pressure liquid chromatography. After further chromatography is performed, solvent is removed in vacuo to obtain refined title product.

Repeating the procedure of this example, but using as starting material in place of the 8-methyl-(8-azabicyclo[3.2.1]oct-3-yl) 4-fluorophenyl methanone, an approximately equivalent amount of 3-hydroxy-8-methyl-(8-azabicyclo[3.2.1]oct-3-yl) phenyl methanone, there is accordingly obtained {8-[3-(2-chloro-10H-phenothiazin-10-yl)propyl]-3-hydroxy-8-azabicyclo[3.2.1]oct-8-yl} phenyl methanone (as a glassy solid).

What is claimed is:

1. A compound which is a free base of the formula:

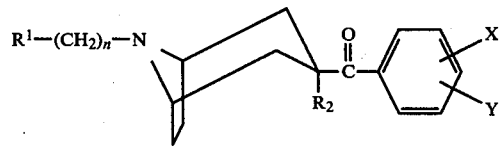

wherein
each of X and Y is independently, a hydrogen atom, fluoro, chloro or bromo, alkyl or alkoxy having from 1 to 4 carbon atoms, or trifluoromethyl, provided that when X and Y are trifluoromethyl, branched alkyl, or branched alkoxy, they are not on adjacent carbon atoms;
n is a whole number of from 1 to 4;
$R^1$ is of type;
(a) a radical of the formula:

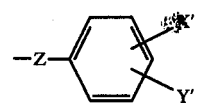

wherein
each of X' and Y' is independently, a hydrogen atom, fluoro, chloro or bromo; alkyl or alkoxy having from 1 to 4 carbon atoms, or trifluoromethyl, provided that when X' and Y' are trifluoromethyl, branched alkyl or branched alkoxy they are not on adjacent carbon atoms, and Z is

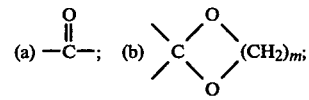

(c) —O—; or (d) a direct bond,
wherein m is 2 or 3;
(b) a radical of the formula:

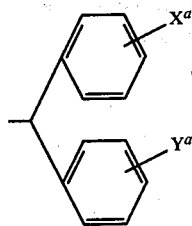

in which $X^a$ and $Y^a$ are, independently, a hydrogen atom or fluoro; or (c) a radical of the formula:

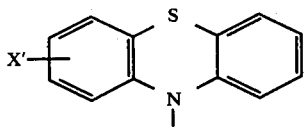

in which
X' is defined above; and,
$R^2$ is
(a) a hydrogen atom;
(b) —OH; or
(c) —O—Si(CH$_3$)$_3$; or a non-toxic acid addition salt thereof.

2. A compound of claim 1 in which $R^1$ is of type (a).
3. A compound of claim 1 in which $R^1$ is of type (b).
4. A compound of claim 1 in which $R^1$ is of type (c).
5. A compound of claim 2, 3 or 4 in which $R^2$ is of type (a).
6. A compound of claim 2, 3 or 4 in which $R^2$ is of type (b).
7. A compound of claim 2, 3 or 4 in which $R^2$ is of type (c).
8. A compound of claim 2 or 3 in which $R^2$ is of type (a) or (b).
9. A compound of claim 4 in which $R^2$ is of type (a) or (b).
10. The compound of claim 2 which is 4-[3-(4-fluorobenzoyl)-8-azabicyclo[3.2.1]oct-8-yl]-1-(4-fluorophenyl)-1-butanone (B-form).
11. The compound of claim 2 which is (8-benzyl-8-azabicyclo[3.2.1]oct-3-yl)4-fluorophenyl methanone (B-form).
12. The compound of claim 3 which is {8-[4,4-bis(4-fluorophenyl)butyl]-3-hydroxy 8-azabicyclo[3.2.1]oct-3-yl}phenyl methanone (B-form).
13. The compound of claim 3 which is {8-[3-(4-methoxyphenoxy)propyl]-3-hydroxy-8-azabicyclo[3.2.1]oct-3-yl}(4-fluorophenyl)methanone (B-form).
14. The compound of claim 7 which is {8-[4,4-bis(4-fluorophenyl)butyl]3-trimethylsiloxy-8-azabicyclo[3.2.1]oct-3-yl}phenyl methanone (B-form).
15. The compound of claim 7 which is ((8-{3-[2-(4-fluorophenyl)-1,3-dioxolan-2-yl]propyl}-3-trimethylsiloxy-8-azabicyclo[3.2.1]oct-3-yl))phenyl methanone (B-form).
16. The compound of claim 4 which is 8[3-(2-chloro-10H-phenothiazin-10-yl)propyl]-8-azabicyclo[3.2.1]oct-3-yl]phenyl methanone (B-form).
17. The compound of claim 4 which is {8-[3-(2-chloro-10H-phenothiazin-10-yl)propyl]-3-hydroxy-8-azabicyclo[3.2.1]oct-3-yl}(4-fluorophenyl)methanone (B-form).
18. A method of tranquillizing a mammal comprising administering to a mammal a anti-psychotic-effective amount of a compound of claim 1.
19. A pharmaceutical composition comprising in unit dose form an inert pharmaceutically-acceptable carrier and a anti-psychotic-effective amount of a compound of claim 1.

* * * * *